(12) United States Patent
Bartelen

(10) Patent No.: US 11,064,883 B2
(45) Date of Patent: Jul. 20, 2021

(54) SLIT LAMP WITH CANTILEVERED BASE

(71) Applicant: Brett Bartelen, Whitehorse (CA)

(72) Inventor: Brett Bartelen, Whitehorse (CA)

(73) Assignee: Brett Bartelen, Whitehorse (CA)

( * ) Notice: Subject to any disclaimer, the term of this patent is extended or adjusted under 35 U.S.C. 154(b) by 273 days.

(21) Appl. No.: 16/265,890

(22) Filed: Feb. 1, 2019

(65) Prior Publication Data

US 2020/0245866 A1  Aug. 6, 2020

(51) Int. Cl.
*A61B 3/135* (2006.01)
*A61B 3/00* (2006.01)

(52) U.S. Cl.
CPC ............ *A61B 3/135* (2013.01); *A61B 3/0083* (2013.01)

(58) Field of Classification Search
CPC .............................. A61B 3/135; A61B 3/0083
USPC .......................................................... 351/214
See application file for complete search history.

(56) References Cited

U.S. PATENT DOCUMENTS

| | | | | |
|---|---|---|---|---|
| 3,830,562 A * | 8/1974 | McGrann | ............... | A61B 3/135 351/214 |
| 4,477,159 A * | 10/1984 | Mizuno | ................... | A61F 9/008 351/205 |
| 4,504,129 A * | 3/1985 | Van Iderstine | .......... | A61B 3/14 351/206 |
| D295,556 S * | 5/1988 | Speaker | ........................ | D24/172 |
| 4,762,409 A * | 8/1988 | Swannie | ................. | A61B 3/135 351/214 |
| 4,925,293 A * | 5/1990 | Hurd | ..................... | A61B 3/0033 351/212 |
| 5,488,443 A * | 1/1996 | Ota | ......................... | A61B 3/135 351/205 |
| 6,275,718 B1* | 8/2001 | Lempert | ................. | A61B 3/107 351/219 |
| 7,052,135 B2* | 5/2006 | Takeda | ................. | A61B 3/0033 351/200 |
| 7,329,003 B2 | 2/2008 | Nicolini | | |
| 7,445,338 B1 | 11/2008 | Beattie | | |
| D612,942 S * | 3/2010 | Verdon-Roe | ................. | D24/172 |
| 7,736,002 B2 | 6/2010 | Small | | |
| 7,819,528 B1 | 10/2010 | Dudee | | |
| 2006/0224147 A1* | 10/2006 | Abe | ........................ | A61F 9/008 606/4 |
| 2007/0236658 A1* | 10/2007 | Nakamura | ........... | A61B 3/0083 351/205 |
| 2011/0001931 A1* | 1/2011 | Davis | ..................... | A61B 3/135 351/214 |
| 2011/0063620 A1* | 3/2011 | Wojtkowski | ........... | A61B 3/135 356/479 |
| 2013/0085369 A1* | 4/2013 | Glovinsky | ............... | A61B 3/16 600/399 |

(Continued)

*Primary Examiner* — Collin X Beatty
(74) *Attorney, Agent, or Firm* — Berenato & White, LLC

(57) ABSTRACT

A base for a slit lamp having a table and a frame mounted to the table, the base comprising a carriage configured to support a biomicroscope, a first elongate member extending horizontally through the carriage, and a second elongate member extending horizontally through the carriage. The carriage is slidable axially along the first elongate member and the second elongate member to move the biomicroscope relative to the frame. The second elongate member provides a stabilizing force on the carriage to counteract an upward force exerted by the carriage and the biomicroscope mounted thereon.

8 Claims, 6 Drawing Sheets

(56) References Cited

U.S. PATENT DOCUMENTS

| | | | |
|---|---|---|---|
| 2016/0095516 A1* | 4/2016 | Nara | A61B 3/0083 351/214 |
| 2016/0106316 A1* | 4/2016 | Tachikawa | A61B 3/0083 351/208 |
| 2016/0374549 A1* | 12/2016 | Xue | A61B 3/135 351/221 |
| 2018/0172969 A1* | 6/2018 | Nakamura | G02B 21/025 |
| 2018/0303335 A1* | 10/2018 | Xue | A61B 3/135 |
| 2019/0099071 A1* | 4/2019 | Ehrmann | G02B 27/0093 |
| 2019/0133435 A1* | 5/2019 | Browne | A61B 3/112 |
| 2019/0209070 A1* | 7/2019 | Cherchi | A61B 3/113 |
| 2020/0245866 A1* | 8/2020 | Bartelen | A61B 3/135 |
| 2020/0323428 A1* | 10/2020 | Tachikawa | A61B 3/102 |

\* cited by examiner

SLIT LAMP WITH CANTILEVERED BASE

TECHNICAL FIELD

The present disclosure relates to a slit lamp provided with an improved slit lamp base. Existing slit lamps may be retrofitted onto the improved slit lamp base to allow the slit lamps to accommodate patients having various body types.

BACKGROUND

U.S. Pat. No. 7,445,338, which issued to Beattie on Nov. 4, 2008, discloses a slit lamp microscope table with a front recess of suitable size to accommodate the torso of the occupant of a wheel chair or an obese individual. With the table set at an appropriate elevation, the handicapped individual can move his or her wheel chair to the vicinity of the table. The wheel chair is rolled toward the table until the user is located with his or her torso in the recess. Once the patient is in position, the table can be lowered to the point at which the arm rests of the table come into contact with the arms on the wheel chair and more positively hold the table and wheel chair in the desired relation.

U.S. Pat. No. 7,329,003, which issued to Nicolini on Feb. 12, 2008, discloses a modified slit lamp assembly light source base and vertical support frame assemblies comprising chin and headrest vertical support legs wherein at least a lower portion of the chin rest vertical supports have been modified in at least a substantially widened fashion. The lower portion of the supports is further modified to jut back or bend away from a seated patient and toward the base of the slit lamp assembly to provide upper body accommodation while at the same time preventing a patient's upper body from encroaching on the base of the slit lamp. The assembly's chin/head support frame is mounted on a pivotal tabletop having a pivotal connection means, wherein the pivotal tabletop comprises a plurality of cut-out shapes each working in cooperative conjunction with the modified assemblies to accommodate obese, large-breasted patients and patients with degenerative back disorders, as well as obese doctors.

SUMMARY

There is provided a base for a slit lamp having a table and a frame mounted to the table, the base comprising a carriage configured to support a biomicroscope, a first elongate member extending horizontally through the carriage, and a second elongate member extending horizontally through the carriage. The carriage is slidable axially along the first elongate member and the second elongate member to move the biomicroscope relative to the frame. The second elongate member provides a stabilizing force on the carriage to counteract an upward force exerted by the carriage and the biomicroscope mounted thereon.

The second elongate member may extend through an elevated portion of the carriage. The first elongate member and the second elongate member may each include a rotatable pinion on each end thereof. The pinions may engage parallel racks to guide movement of the carriage and the biomicroscope relative to the frame. The parallel racks may be formed in housings mounted on the table.

A first pair of the parallel racks may be mounted on bottoms of the housings and a second pair of the parallel racks may be mounted on tops of the housings. The pinions of the first elongate member may engage the first pair of the parallel racks and the pinions of the second elongate member may engage the second pair of the parallel racks.

A first pair of the housings may be mounted on a top surface of the table and a second pair of the housings may be supported above the top surface of the table by spaced-apart, vertical shafts extending through the housings. The pinions of the first elongate member may engage the parallel racks formed in the first pair of the housings and the pinions of the second elongate member may engage the parallel racks formed in the second pair of the housings.

Each of the vertical shafts may have a threaded portion which engages with a corresponding internally threaded portion of the housings. There may be knobs coupled to the vertical shafts. The knobs may be rotatable to adjust a distance between the housings and the top surface of the table.

There is also provided a slit lamp comprising a table and a frame mounted to the table. The frame has spaced-apart vertical support members, and a forehead rest and a chin rest extending between the vertical support members. The slit lamp further includes a base mounted on the table. The base has a carriage configured to support a biomicroscope, a first elongate member extending horizontally through the carriage, and a second elongate member extending horizontally through the carriage. The carriage is slidable axially along the first elongate member and the second elongate member to move the biomicroscope relative to the frame. The second elongate member provides a stabilizing force on the carriage to counteract an upward force exerted by the carriage and the biomicroscope mounted thereon. The frame may have curved lower portions where the frame meets the table.

DESCRIPTION OF SPECIFIC EMBODIMENTS

Figure 1:
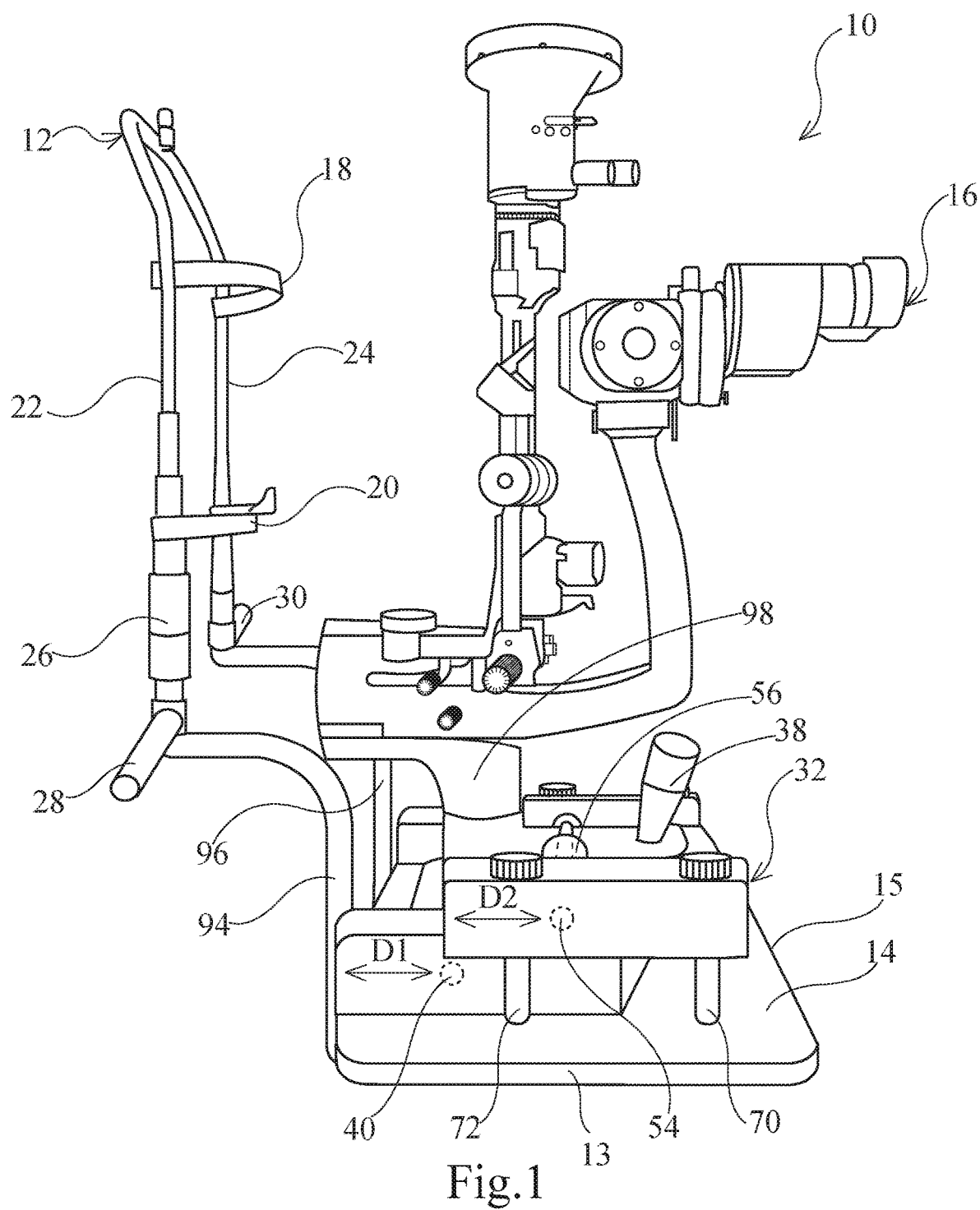
FIG. 1 is a side perspective view of a first embodiment of a slit lamp provided with an improved slit lamp base.

Referring to the drawings and first to FIG. 1, there is shown a first embodiment of a slit lamp 10. The slit lamp 10 includes a headrest frame 12 mounted on a table 14. The table 14 supports a biomicroscope 16. There is a forehead rest 18 and a chin rest 20 extending between parallel, spaced-apart vertical rods 22 and 24 of the headrest frame 12. The forehead rest 18 and the chin rest 20 support a patient's head during examination and allow for proper placement of the patient's head at the correct distance from the biomicroscope 16. The height of the chin rest 20 may be adjusted by rotating a sleeve 26 disposed on the vertical rod 22. The slit lamp 10 also includes handles 28 and 30 for the patient to hold onto during examination. The slit lamp 10 thus far described is conventional. However, the slit lamp 10 includes an improved base 32 which supports the biomicroscope 16. The base 32 utilizes a cantilevered dual-axle design to reduce the footprint of the base 32, and thus the size of the table 14, as will be described below.

Figure 2:
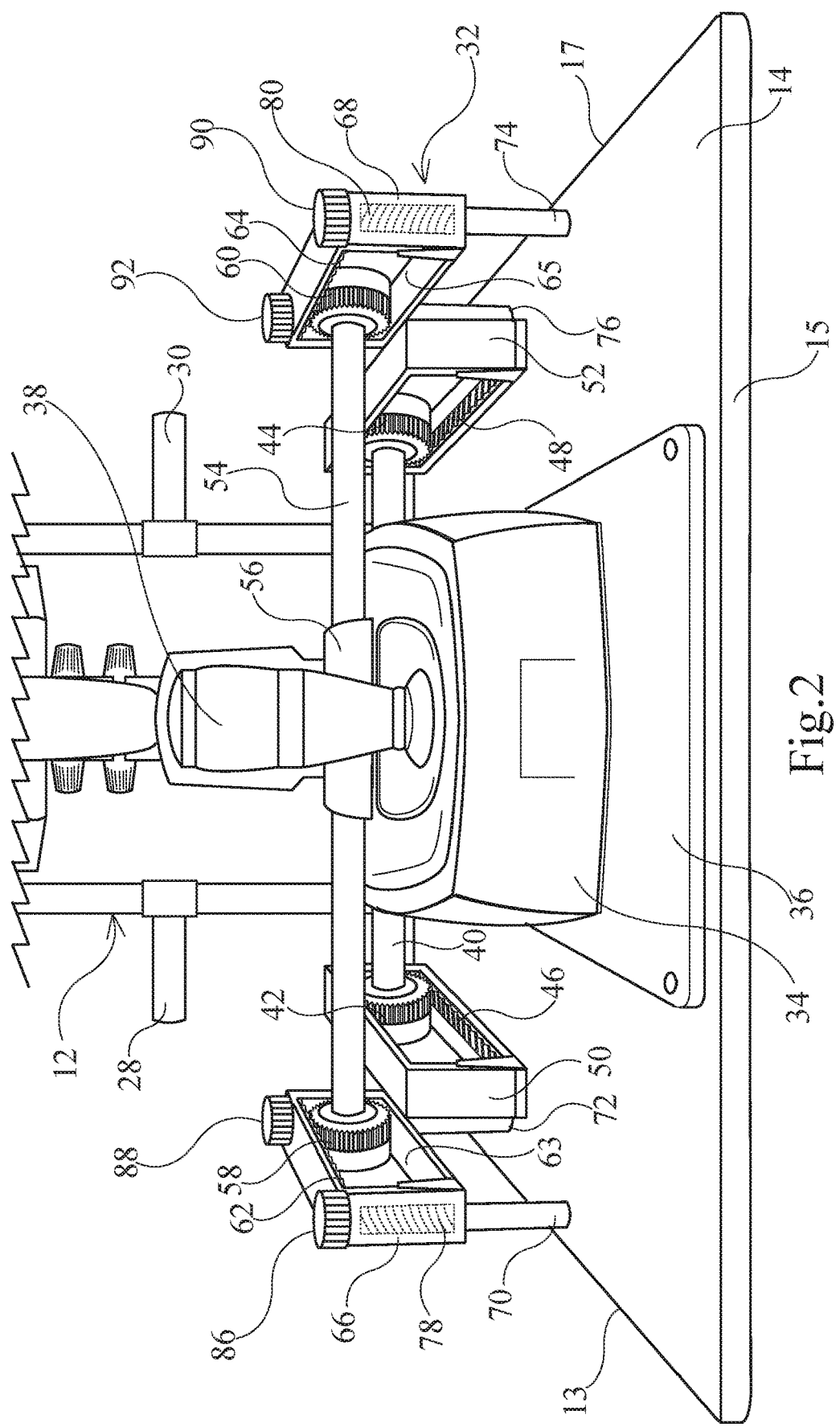
FIG. 2 is a rear perspective view of the slit lamp base of FIG. 1.

As best shown in FIG. 2, the base 32 includes a carriage 34 which is mounted to be moveable over the table 14 relative to the headrest frame 12. There is a fiction pad 36 mounted on the table 14 between the carriage 34 and the table 14 to facilitate movement of the carriage 34 over the table 14. The carriage 34 contains a joystick 38 which allows a physician to maneuver the biomicroscope 16 during examination in order to focus on the patient's eye. There is a first axle 40 extending horizontally through the carriage 34. The first axle 40 has pinions 42 and 44 on opposite ends thereof. The pinions 42 and 44 are rotatable and ride on parallel racks 46 and 48 formed in housings 50 and 52 mounted on the table 14. There is also a second axle 54 extending horizontally through the carriage 34. In this example, the second axle 54 extends horizontally through a sleeve 56 extending upwardly from the carriage 34. The second axle 54 has pinions 58 and 60 on opposite ends thereof. The pinions 58 and 60 are rotatable and ride on parallel racks 62 and 64 formed in housings 66 and 68 supported on the table 14. The housings 66 and 68 are sized to provide clearance between the pinions 58 and 60 and respective bottoms 63 and 65 of the housings 66 and 68.

The carriage 34 of the slit lamp 10 has a smaller footprint compared to carriages of conventional slit lamps. In a conventional slit lamp having one axle, if the size of the carriage is reduced, the center of gravity shifts, which can cause the biomicroscope mounted on the carriage to tip over. Therefore, the carriage has to be sufficiently large to support the weight of the biomicroscope. With the slit lamp 10, an upward force exerted by the biomicroscope 16 and the carriage 34, due to the smaller size of the carriage 34, is counteracted by the second axle 54. The pinions 58 and 60 of the second axle 54 engage the racks 62 and 64 extending downwardly from the tops of the housings 66 and 68 to provide a counterforce to the upward force exerted by the biomicroscope 16 and the carriage 34. This inhibits the biomicroscope 16 from tipping over when mounted on the smaller carriage 34. The smaller carriage 34 allows the size of the table 14 to be reduced which in turn allows for more space to accommodate patients' bodies.

Figure 3:
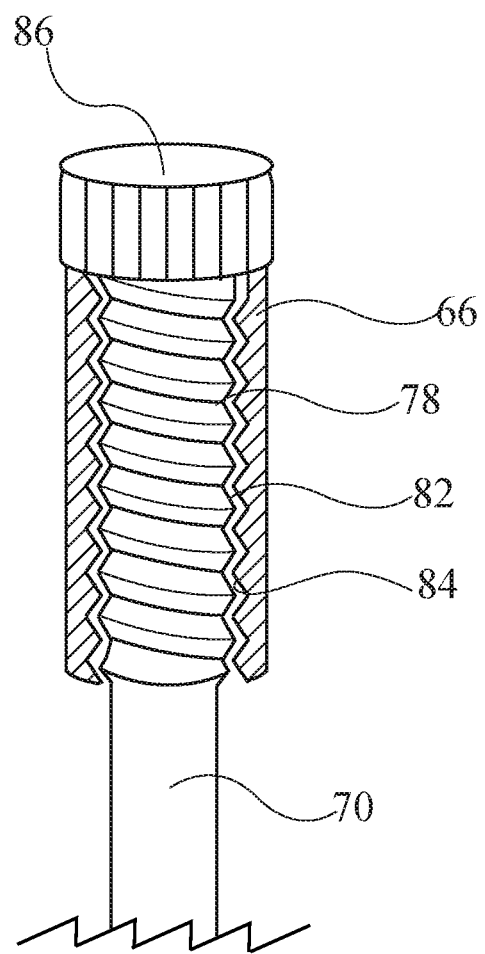
FIG. 3 is a cross-sectional view of a vertical shaft threadedly engaging a housing of a rack and pinion mechanism of the slit lamp base of FIG. 1.

The housings 66 and 68 are supported above the table 14 by spaced-apart vertical shafts as shown by spaced-apart vertical shafts 70 and 72 extending through the housing 66 and spaced-apart vertical shafts 74 and 76 extending through the housing 68. Each of the vertical shafts has a threaded portion as shown by a threaded portion 78 of the vertical shaft 70 and a threaded portion 80 of the vertical shaft 74. The threaded portion of each of the vertical shafts has external threads which engage with internal threads of the housings, as shown in FIG. 3 by external threads 82 of the threaded portion 78 of the vertical shaft 70 engaging with internal threads 84 of the housing 66. Referring back to FIG. 2, there is a plurality of knurled knobs 86, 88, 90 and 92, each coupled to the top of one of the vertical shafts 70, 72, 74 and 76. The knurled knobs 86, 88, 90 and 92 can be rotated to adjust the distance between the housings 66 and 68 and the table 14, thereby adjusting the downward pressure that the second axle 54 applies on the carriage 34. This allows the physician to regulate the amount of friction between the friction pad 36 and the bottom of the carriage 34 and the joystick 38.

Figure 4:
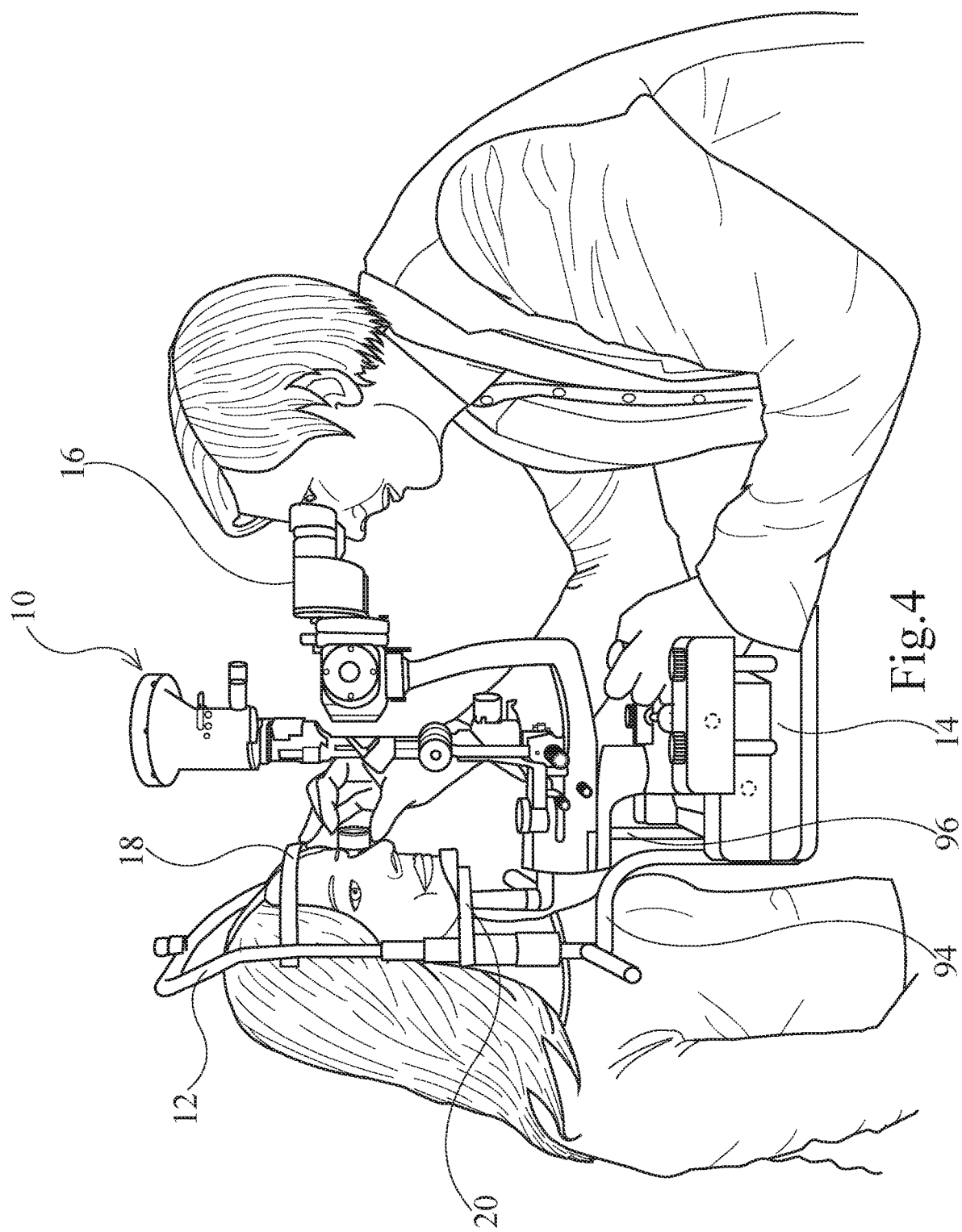
FIG. 4 is a side perspective view of the slit lamp of FIG. 1 shown in use with a patient and a doctor during an eye examination.

As shown in FIG. 4, the headrest frame 12 has curved lower portions 94 and 96 where the frame 12 meets the table 14. The lower portions 94 and 96 are generally L-shaped in this example and extend horizontally away from the table 14 to provide room underneath for a patient's torso. This additional room may be beneficial in situations where the patient has a larger or shorter body type. Accordingly, the slit lamp 10 can accommodate a greater range of patient body types. The curved shape of the lower portions 94 and 96 also ensures that the forehead rest 18 and the chin rest 20 are positioned at the correct distance from the biomicroscope 16 even with the smaller size of the table 14.

Referring back to FIGS. 1 and 2, the carriage 34 is slidable or translatable axially along the first axle 40 and the second axle 54 to move the biomicroscope 16 over the table 14 from one side 13 to the opposite side 17. The pinions 42, 44, 58 and 60 also ride along their respective racks 46, 48, 62 and 64 to move the carriage 34 and the biomicroscope 16 forward and backward over the table 14. Movement of the carriage 34 over the table 14 and relative to the headrest frame 12 can be controlled by actuating the joystick 38. The pinions 42 and 44 of the first axle 40 have a travel distance D1 which is equal to a travel distance D2 of the pinions 58 and 60 of the second axle 54. The first axle 40 is positioned substantially below a post 98 which connects the biomicroscope 16 to the carriage 34. The second axle 54 is positioned closer to the joystick 38 than to the first axle 40 to provide greater stability when actuating the joystick 38 in the forward or backward direction. In this example, the second axle 54 is positioned between the joystick 38 and the first axle 40. However, in other examples, the second axle 54 may be positioned between the joystick 38 and a rear 15 of the table 14.

Figure 5:
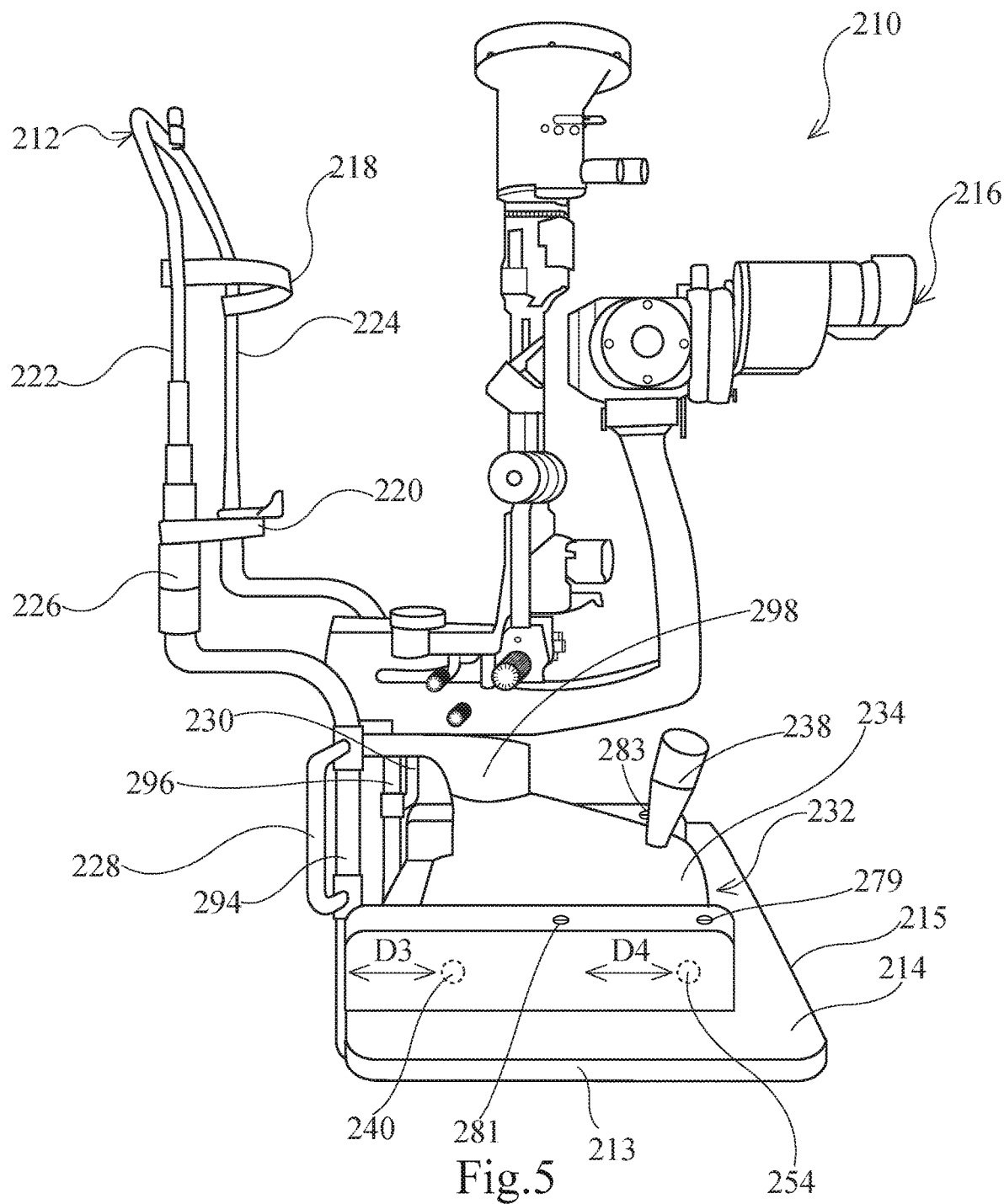
FIG. 5 is a side perspective view of a second embodiment of a slit lamp provided with an improved slit lamp base.
Figure 6:
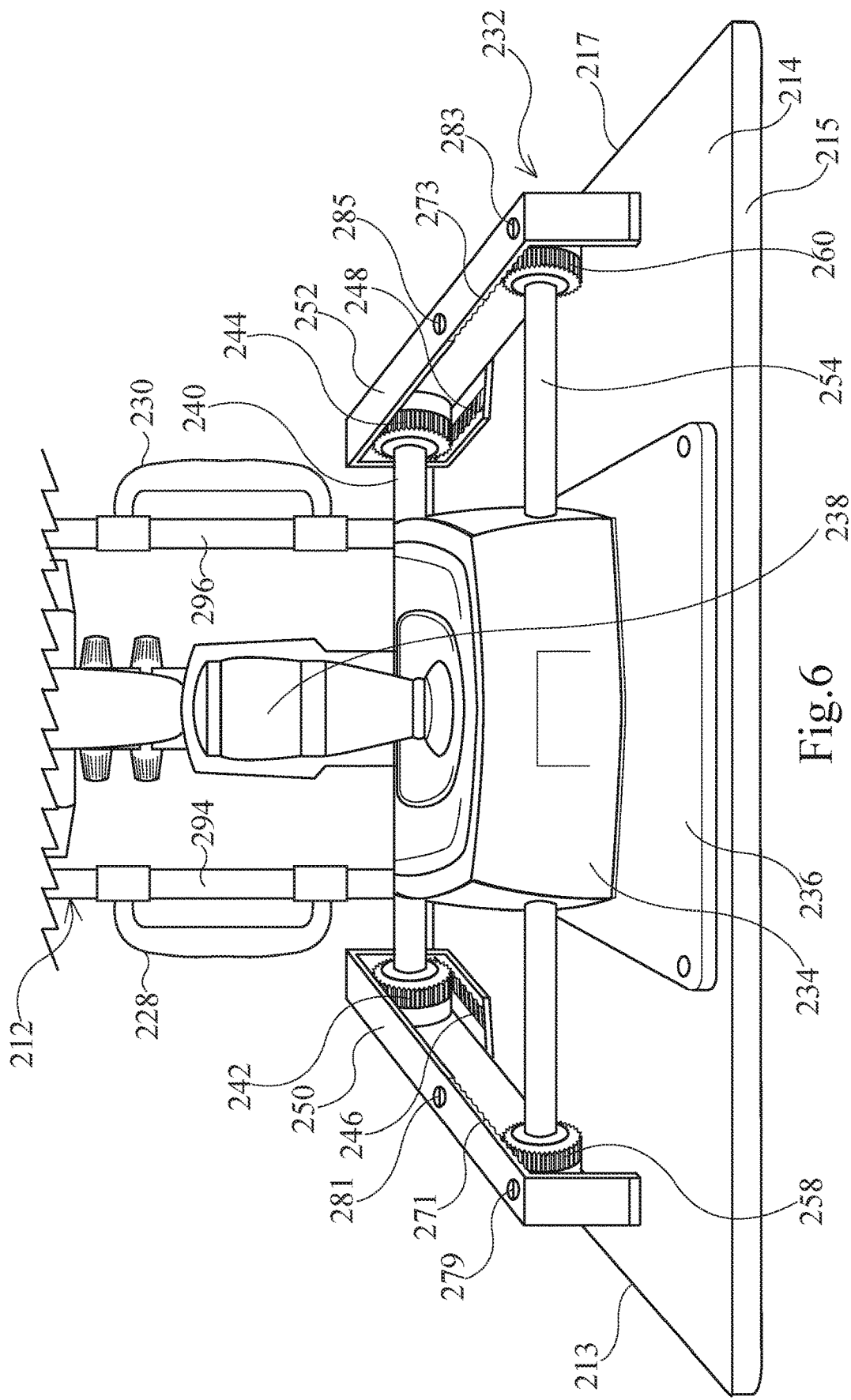
FIG. 6 is a rear perspective view of the slit lamp base of FIG. 5.

FIGS. 5 and 6 show a second embodiment of a slip lamp 210. Like parts have like numbers and functions as the slit lamp 10 described above and shown in FIGS. 1 to 4 except in the 200 series. The slit lamp 210 includes a headrest frame 212 mounted on a table 214. The table 214 supports a biomicroscope 216. There is a forehead rest 218 and a chin rest 220 extending between parallel, spaced-apart vertical rods 222 and 224 of the headrest frame 212. There are also handles 228 and 230 mounted on curved lower portions 294 and 296 of the headrest frame 212 where the frame 212 meets the table 214. In this example, the handles 228 and 230 are generally U-shaped. The slit lamp 210 further includes a base 232 which supports the biomicroscope 216.

As best shown in FIG. 6, the base 232 includes a carriage 234 which contains a joystick 238. The carriage 234 is mounted to be moveable over the table 214 relative to the headrest frame 212. There is a first axle 240 extending horizontally through the carriage 234. The first axle 240 has pinions 242 and 244 on opposite ends thereof. The pinions 242 and 244 are rotatable and ride on parallel racks 246 and 248 formed in housings 250 and 252 mounted on the table 214. There is also a second axle 254 extending horizontally through the carriage 234. The second axle 254 has rotatable pinions 258 and 260 on opposite ends thereof. There are racks 271 and 273 extending downwardly from the tops of the housings 250 and 252. The racks 271 and 273 engage the pinions 258 and 260 of the second axle 254 to counteract an upward force exerted by the biomicroscope 216 and the carriage 34, due to the smaller size of the carriage 234. Screws 279, 281, 283 and 285 in the housings 250 and 252 can be adjusted to regulate the downward pressure applied by the racks 271 and 273 on the pinions 258 and 260 of the second axle 254. In this way, the downward force that the second axle 54 applies on the carriage 34 can be adjusted. This allows the physician to regulate the amount of friction between the bottom of the carriage 234 and the joystick 238, and a friction pad 236 mounted on the table 214.

The bottom racks 246 and 248 and the top racks 271 and 273 extend partially along the lengths of the housings 250 and 252 such that a travel distance D3 of the pinions 242 and 244 of the first axle 240 is equal to a travel distance D4 of the pinions 258 and 260 of the second axle 254 as shown in FIG. 5. In this example, the second axle 254 is positioned between the joystick 238 and a rear 215 of the table 214. However, in other examples, the second axle 254 may be positioned between the joystick 238 and the first axle 240.

It will be understood by a person skilled in the art that many of the details provided above are by way of example only, and are not intended to limit the scope of the invention which is to be determined with reference to the following claims.

What is claimed is:

1. A base for a slit lamp having a table and a frame mounted to the table, the base comprising:
    a carriage configured to support a biomicroscope;
    a first elongate member extending horizontally through the carriage; and
    a second elongate member extending horizontally through the carriage;
    wherein the carriage is slidable axially along the first elongate member and the second elongate member to move the biomicroscope relative to the frame;
    wherein the second elongate member provides a stabilizing force on the carriage to counteract an upward force exerted by the carriage and the biomicroscope mounted thereon;
    wherein the first elongate member and the second elongate member each includes a rotatable pinion on each end thereof, the pinions engaging parallel racks to guide movement of the carriage and the biomicroscope relative to the frame;
    wherein the parallel racks are formed in housings mounted on the table;
    wherein a first pair of the parallel racks is mounted on bottoms of the housings and a second pair of the parallel racks is mounted on tops of the housings, and
    wherein the pinions of the first elongate member engage the first pair of the parallel racks and the pinions of the second elongate member engage the second pair of the parallel racks.

2. A base for a slit lamp having a table and a frame mounted to the table, the base comprising:
    a carriage configured to support a biomicroscope;
    a first elongate member extending horizontally through the carriage; and
    a second elongate member extending horizontally through the carriage;
    wherein the carriage is slidable axially along the first elongate member and the second elongate member to move the biomicroscope relative to the frame;
    wherein the second elongate member provides a stabilizing force on the carriage to counteract an upward force exerted by the carriage and the biomicroscope mounted thereon;
    wherein the first elongate member and the second elongate member each includes a rotatable pinion on each end thereof, the pinions engaging parallel racks to guide movement of the carriage and the biomicroscope relative to the frame;
    wherein the parallel racks are formed in housings mounted on the table;
    wherein a first pair of the housings is mounted on a top surface of the table and a second pair of the housings is supported above the top surface of the table by spaced-apart, vertical shafts extending through the housings, and
    wherein the pinions of the first elongate member engaging the parallel racks are formed in the first pair of the housings and the pinions of the second elongate member engaging the parallel racks are formed in the second pair of the housings.

3. The slit lamp as claimed in claim 2, wherein each of the vertical shafts has a threaded portion which engages with a corresponding internally threaded portion of the housings.

4. The slit lamp as claimed in claim 3, further including knobs coupled to the vertical shafts, the knobs being rotatable to adjust a distance between the housings and the top surface of the table.

5. A slit lamp, comprising:
    a table and a frame mounted to the table, the frame having spaced-apart vertical support members, and a forehead rest and a chin rest extending between the vertical support members; and
    a base mounted on the table, the base having:
        a carriage configured to support a biomicroscope,
        a first elongate member extending horizontally through the carriage, and
        a second elongate member extending horizontally through the carriage, wherein the carriage is slidable axially along the first elongate member and the second elongate member to move the biomicroscope relative to the frame;
        wherein the second elongate member provides a stabilizing force on the carriage to counteract an upward force exerted by the carriage and the biomicroscope mounted thereon;
    wherein the first elongate member and the second elongate member each includes a rotatable pinion on each end thereof, the pinions engaging parallel racks to guide movement of the carriage and the biomicroscope relative to the frame;
    wherein the parallel racks are formed in housings mounted on the table;
    wherein a first pair of the parallel racks is mounted on bottoms of the housings and a second pair of the parallel racks is mounted on tops of the housings, and
    wherein the pinions of the first elongate member engage the first pair of the parallel racks and the pinions of the second elongate member engage the second pair of the parallel racks.

6. A slit lamp, comprising:
    a table and a frame mounted to the table, the frame having spaced-apart vertical support members, and a forehead rest and a chin rest extending between the vertical support members; and
    a base mounted on the table, the base having:
        a carriage configured to support a biomicroscope,
        a first elongate member extending horizontally through the carriage, and
        a second elongate member extending horizontally through the carriage, wherein the carriage is slidable axially along the first elongate member and the second elongate member to move the biomicroscope relative to the frame;
        wherein the second elongate member provides a stabilizing force on the carriage to counteract an upward force exerted by the carriage and the biomicroscope mounted thereon;
    wherein the first elongate member and the second elongate member each includes a rotatable pinion on each end thereof, the pinions engaging parallel racks to guide movement of the carriage and the biomicroscope relative to the frame;

wherein the parallel racks are formed in housings mounted on the table;

wherein a first pair of the housings is mounted on a top surface of the table and a second pair of the housings is supported above the top surface of the table by spaced-apart, vertical shafts extending through the housings, and wherein the pinions of the first elongate member engaging the parallel racks are formed in the first pair of the housings and the pinions of the second elongate member engaging the parallel racks are formed in the second pair of the housings.

7. The slit lamp as claimed in claim 6, wherein each of the vertical shafts has a threaded portion which engages with a corresponding internally threaded portion of the housings.

8. The slit lamp as claimed in claim 7, further including knobs coupled to the vertical shafts, the knobs being rotatable to adjust a distance between the housings and the top surface of the table.

\* \* \* \* \*